US007659443B2

(12) United States Patent
Kono et al.

(10) Patent No.: US 7,659,443 B2
(45) Date of Patent: Feb. 9, 2010

(54) METHOD OF CONSTRUCTING NUCLEUS-IMPLANTED EGG, PARTHENOGENETIC EMBRYO AND PARTHENOGENETIC MAMMAL

(75) Inventors: Tomohiro Kono, Tokyo (JP); Yayoi Obata, Tokyo (JP); Manabu Kawahara, Tokyo (JP)

(73) Assignee: Tokyo University of Agriculture Educational Corporation, Tokyo (JP)

( * ) Notice: Subject to any disclaimer, the term of this patent is extended or adjusted under 35 U.S.C. 154(b) by 0 days.

(21) Appl. No.: 12/213,385

(22) Filed: Jun. 18, 2008

(65) Prior Publication Data

US 2009/0031437 A1     Jan. 29, 2009

Related U.S. Application Data

(63) Continuation-in-part of application No. 10/566,724, filed as application No. PCT/JP2004/011491 on Aug. 4, 2004, now abandoned.

(30) Foreign Application Priority Data

Aug. 5, 2003   (JP)   ............... 2003-286543
Jun. 29, 2007  (JP)   ............... 2007-171707

(51) Int. Cl.
    C12N 15/00   (2006.01)
    A01K 67/027  (2006.01)
(52) U.S. Cl. .................. 800/24; 800/14; 800/25
(58) Field of Classification Search ............ 800/24
    See application file for complete search history.

(56) References Cited

U.S. PATENT DOCUMENTS

2006/0212948 A1    9/2006   Kono et al.

FOREIGN PATENT DOCUMENTS

| EP | 1 661 456 A   | 5/2006 |
| EP | 1661456 A     | 5/2006 |
| WO | WO-01/30978 A1 | 5/2001 |

OTHER PUBLICATIONS

Denning and Priddle, 2003, New frontiers in gene targeting and cloning: success, application and challenges in domestic animals and human embryonic stem cells Reproduction 126:1-11.*
Smith, KR, 2002, Gene transfer in higher animals: theoretical considerations and key concepts, Journal of Biotechnology, 99:1-22.*
Kawahara, M et al, Sep. 2007, High-frequency generation of viable mice from engineered bi-maternal embryos, Nature Biotechnology, 25:104-1050.*
Kono et al., Paternal Dual Barrier by Ifg2-H19 and DIk1-Gt12 to Parthenogenesis in mice. Ernest Schering Research Foundation Workshop Springer—Verlag Berlin, Heidelberger Platz 3, D-14197 Berlin, Germany Series : Ernst Schering Research Foundation Workshop (ISSN 0947-6075 (Print)), 2006, pp. 23-33. XP-009107588. & Workshop on Stem Cells in Reproduction and in the Brain; Kobe, Japan; Sep. 1-3, 2005 ISSN: 3-540-31436-9 (H) p. 29, paragraph 3-p. 30, paragraph 2.
Wu et al., Regulated expression of two sets of paternally imprinted genes is necessary for mouse parthenogenetic development to term, Reproduction, vol. 131, No. 3, 2006, pp. 481-488. XP 002501736, ISSN: 1470-1626.
Kawahara et al., Nature Biotechnology, vol. 25, No. 9, Sep. 2007, pp. 1045-1050. XP-002501737.
Kawahara et al., Nature Protocols, Nature Publishing Group, UK, vol. 3, No. 2, 2008, pp. 197-209. XP001538923.
T. Kono, Cytogenetic and Genome Research, vol. 113, No. 1-4, 2006, pp. 31-35, XP009107587.
Kono, T. et al., Nature, Apr. 22, 2004, vol. 428 (6985), pp. 860 to 864.
Sotomaru, T. et al., J. Biol. Chem., Apr. 5, 2002 vol. 277 (14), pp. 12474 to 12478.
Kono T. et al., Dev, Biol., Mar. 15, 2002, vol. 243 (2), pp. 294 to 300.
Sotomaru Y. et al., J. Biol. Chem., Jul. 13,. 2001, vol. 276 (28), pp. 26694 to 26698.
Obata, Y. et al., Development, 1998 Apr., vol. 125 (8), pp. 1553 to 1560.
Escriba, MJ et al., Theriogenology, Feb. 1, 2001, vol. 55 (3), pp. 771 to 784.
Tomohiro Kono et al., Protein, Nucleic acid and Enzyme, 1998, vol. 43 (4), pp. 565 to 572.
Kono et al., "Proteins, Nucleic Acid and Enzymes", Genomic Imprinting During Oogenesis and Embryonic Development, vol. 43, No. 4, (1998), pp. 565-574.
Kono, et al., "Birth of Parthenogenetic Mice That Can Develop to Adulthood", Nature, vol. 428, No. 6935, pp. 860-864, Apr. 22, 2004.
P.A. Leighton, et al., "Disruption of Imprinting Caused by Deletion of the H19 Gene Region in Mice", Nature 375, pp. 34-39, 1995.
Schmidt, J.V., et al., "The Dlk1 and GtI2 Genes are Linked and Reciprocally Imprinted", Genes Dev. 14 1997-2002, 2000.
S.J. Abbondanzo, et al., "Derivation of Embryonic Stem Cell Lines", Methods in Enzymology, vol. 225, pp. 803-890, 1993.

(Continued)

Primary Examiner—Valarie Bertoglio
(74) Attorney, Agent, or Firm—Birch, Stewart, Kolasch & Birch, LLP (57) ABSTRACT

Disclosed is a method for constructing a nucleus-implanted egg, a parthenogenetic embryo and for producing a parthenogenetic mammal each having 2 haploid genome sets originating in mammalian ova, and provides methods of constructing a nucleus-implanted egg having a haploid genome set derived from primitive ovarian follicle egg (ng ovum) and a haploid genome set from MII phase (second meiosis metaphase) egg (fg ovum), a parthenogenetic embryo and a parthenogenetic mammal, including steps (1) introducing ng ovum into a nucleus-deleted deleted germinal vesicle stage (GV) egg, developing the obtained egg to MII phase by in vitro maturing and culturing to prepare a first nucleus-implanted egg, and (2) extracting MII phase chromosome from the first nucleus-implanted egg and introducing it into other fg ovum to prepare a second nucleus-implanted egg, wherein a ng or fg ovum from which an imprinted gene undergoing epigenetic modification during sperm generation is used.

10 Claims, 3 Drawing Sheets

OTHER PUBLICATIONS

Y. Sotomaru, et al., "Unregulated Expression of the Imprinted Genes H19 and Igf2r in Mouse Uniparental Fetuses", J. Bio. Chem., vol. 277 (14), pp. 12474-12478, Apr. 5, 2002.
Kono, et al., "Mouse Parthenogenetic Embryos With Monoallelic *H19* Expression Can Develop to Day 17.5 of Gestation", Dev. Biol., vol. 243(2), pp. 294-300, Mar. 15, 2002.
Y. Sotomaru, et al., "Disruption of Imprinted Expression of *U2afbp-rs/U2af1-rs1* Gene in Mouse Parthenogenetic Fetuses", J. Biol, Chem., vol. 276(28), pp. 26694-26696, Jul. 13, 2001.
Obata, et al., "Disruption of Primary Imprinting Durign Oocyte Growth Leads to the Modified Expression of Imprinted Genes During Embryogenesis", vol. 125(8), pp. 1553-1560, Apr. 1998.
Escriba, et al., "Reconstruction fo the Heteroparental Diploid Condition in Rabbit Zygotes By Nuclear Transfer", Theriogenology, vol. 55 (3), pp. 771-784, Feb. 1, 2001.
Sasaki et al., Development, vol. 121, No. 12, pp. 4195-4202 (1995).
Kono et a., Nature Genetics, vol. 13, No. 1, pp. 91-94 (1996).
Nikaido et al., Genome Research, vol. 13, No. 6b, pp. 1402-1409 (Jun. 2003).
Kono et al., Paternal Dual Barrier by Ifg2-H19 and Dlk1-Gtl2 to Parthenogenesis in mice. Ernest Schering Research Foundation Workshop Springer—Verlag Berlin, Heidelberger Platz 3, D-14197 Berlin, Germany Series : Ernst Schering Research Foundation Workshop (ISSN 0947-6075 (Print)), 2006, pp. 23-33. XP-009107588. & Workshop on Stem Cells in Reproduction and in the Brain; Kobe, Japan; Sep. 1-3, 2005 ISSN: 3-540-31436-9 (H) p. 29, paragraph 3- p. 30, paragraph 2.
Wu et al., Regulated expression of two sets of paternally imprinted genes is necessary for mouse parthenogenetic development to term, Reproduction. vol. 131, No. 3, 2006, pp. 481-488. XP 002501736, ISSN: 1470-1626.
Kawahara et al., Nature Biotechnology, vol. 25, No. 9, Sep. 2007, pp. 1045-1050. XP-002501737.
Kawahara et al., Nature Protocols, Nature Publishing Group, UK, vol. 3 , No. 2, 2008, pp. 197-209. XP001538923.
T. Kono, Cytogenetic and Genome Research, vol. 113, No. 1-4, 2006, pp. 31-35, XP009107587.

* cited by examiner

METHOD OF CONSTRUCTING NUCLEUS-IMPLANTED EGG, PARTHENOGENETIC EMBRYO AND PARTHENOGENETIC MAMMAL

This is a continuation-in-part of application Ser. No. 10/566,724, filed Feb. 2, 2006, now abandoned, which is a PCT national stage application of PCT/JP2004/011491, filed Aug. 4, 2004, now abandoned, which claims the benefit of Japanese application No. 2003-286543 filed Aug. 5, 2003 and Japanese application No. 2007-171707 filed Jun. 29, 2007.

TECHNICAL FIELD

The present invention relates to a method for constructing a nucleus-implanted egg. More specifically, it relates to a method of constructing a nucleus-implanted egg produced from maternal genomes alone. The present invention also relates to a method for constructing a parthenogenetic embryo from a nucleus-implanted egg. Further, the present invention relates to a method for producing a parthenogenetic mammal from the above parthenogenetic embryo.

TECHNICAL BACKGROUND

Mammals perform ontogeny by fertilization of ova and sperm, and the ontogeny is never completed by ova alone, which means that the genomes of sperm and eggs are vitally different in function. It is said that the above functional difference is due to the existence of groups of genes (imprinted genes) which are identical but exhibit entirely different expressions depending upon whether they are from sperm or they are from ovum as a result of chemical DNA modification imprinted posteriori during the generation of germ cells. In fact, oocytes of neonates have not undergone the above gene modification, and a number of genes exhibit gene expression patterns like those derived from sperm.

For analyzing the expression patterns of imprinted genes, a method of constructing a nucleus-implanted ovum from a genome derived from an oocyte of a neonate of a mouse and a genome of an ovum derived from a maturated female mouse has been proposed. (see "Genomic Imprinting during Oogenesis and Embryonic Development" by Tomihiro Kono, Proteins, Nucleic Acid and Enzymes Vol. 43, No. 4 (1998), pp. 267-274.) The above method comprises the steps of (1) introducing neonate oocyte (ng ovum) into a nucleus-deleted egg at a germinal vesicle stage (GV stage) and then developing the oocyte to an MII phase (second meiosis metaphase) by in vitro culture for maturation to prepare a first nucleus-implanted egg, and (2) extracting MII phase chromosomes from the above first nucleus-implanted egg and introducing it into other MII phase egg (fg ovum) to prepare a second nucleus-implanted egg. The second nucleus-implanted egg obtained by this method has a haploid genome set derived from the ng ovum and a haploid genome set derived from the fg ovum.

Neonate oocytes (ng ova) do not resume any meiosis by nature until they reach the last stage (mouse ova having a diameter of 60 μm) of ovum growth process, and their cell cycles are at a stop at a diplotene stage in the beginning phase of the first meiosis. We have found that when the above neonate oocyte (ng ovum) whose cell cycle is at a stop is introduced into the cytoplasm of a fully grown oocyte, it resumes meiosis, and the above method has been accordingly proposed.

The introduced gene derived from the ng ovum has not undergone chemical DNA modification imprinted posteriori during the ovum growth period, and it is expected that the second nucleus-implanted egg will be a useful material for analyzing the expression control of an imprinted gene. It has been confirmed that parthenogenetic embryo from the above second nucleus-implanted egg develops to a fetus at day 13.5 of gestation, which fetus morphologically normal comparison with a fetus derived from a fertilized egg. However, its growth thereafter could not been confirmed.

DISCLOSURE OF THE INVENTION

It is an object of the present invention to provide a method for constructing a nucleus-implanted egg that is a nucleus-implanted egg having 2 (two) haploid genome sets derived from mammal ova and is able to grow up to adulthood, a method for constructing a parthenogenetic embryo from the above nucleus-implanted egg and a method for producing a parthenogenetic mammal from the above parthenogenetic embryo.

The gene of the ng ovum for use in the method for constructing a second nucleus-implanted egg, described in the above-noted document, has not undergone chemical DNA modification imprinted posteriori during an ovum growth period and is close to a gene derived from sperm, but it differs from the gene derived from sperm.

We have made diligent studies for bringing a genomic gene of the second nucleus-implanted egg having 2 haploid genome sets derived from ova close into a genomic gene in the fertilization of sperm and ovum and, as a result, have arrived at the present invention by finding the use, as one of the haploid genome sets derived from ova, of a gene from which an imprinted gene that is to undergo gene modification posteriori during spermatogenesis is deleted.

That is, in mammals, identical genes or alleles are arranged in the same sequence on homologous chromosomes derived from paternal and maternal genes, genic expressions are equally exhibited from biparental alleles to take part in gene expressions of individuals.

However, some genes exhibit paternal expressions and some genes exhibit maternal expressions. For example, H19 gene is a gene that regulates the expression of IGF2 (insulin like growth factor II) that is an embryo growth factor, and it is expressed from a maternal gene but is not expressed from a paternal gene. That is because the H19 gene undergoes posterior gene modification during the generation of sperm and is inhibited from paternal expression. Such a gene is called an imprinted gene.

On the other hand, IGF2 gene is expressed from a paternal gene but is not expressed from a maternal gene. That is because the IGF2 gene and the H19 gene have in common an enhancer (gene expression enhancing sequence) located in a downstream to the H19 gene. This enhancer generally works dominantly over the H19 gene, and when it undergoes gene modification posteriori during the generation of sperm, it can no longer work on the H19 gene, and it comes to work on the IGF2 gene. As a result, there is established a relationship in which the expression of the H19 gene from a paternal gene is inhibited and the IGF2 gene is expressed from a paternal gene.

In the general fertilization of sperm and ovum, the H19 gene is expressed from a maternal gene and the IGF2 gene is expressed from a paternal gene, whereby normal embryogenesis is performed. In case that parthenogenesis between ovum and ovum is conducted like the present invention and when the genes of both of the ova are derived from maternal genes, it is predicted that H19 gene alone, which is expressed from a maternal gene, is expressed, and that IGF2 gene, which is expressed from a paternal gene, is not expressed.

We have found, however, that when one of H19 genes from ova is deleted for the parthenogenesis of ovum and ovum, the IGF gene which is expressed from a paternal gene by nature is expressed from a gene derived from the ovum (maternal gene) to perform normal embryogenesis and generation of a mammal, and the present invention has been accordingly completed.

According to the present invention, (call as 'First invention' hereinafter) there is provided a method for constructing a nucleus-implanted egg of a mammal, the nucleus-implanted egg having a haploid genome set derived from ng ovum and a haploid genome set derived from fg ovum, which comprises the steps of (1) introducing a primitive ovarian follicle egg (ng ovum) into a nucleus-deleted egg in a germinal vesicle stage (GV stage egg) and then developing them to MII phase (second meiosis metaphase) by in vitro culture for development to prepare a first nucleus-implanted egg, and (2) extracting all of MII phase chromosome from said first nucleus-implanted egg and introducing it into other MII phase egg (fg ovum) to prepare a second nucleus-implanted egg, wherein ovum from which an imprinted gene that undergoes gene modification posteriori during the generation of sperm is deleted is used as the ng ovum or fg ovum.

First invention includes a method for constructing a parthenogenetic embryo, which comprises activating said second nucleus-implanted egg and developing the same in vitro culture for development.

First invention also includes a method for producing a parthenogenetic mammal, which comprises implanting said parthenogenetic embryo in the uterus of a female mammal and growing the same.

According to First invention, there is provided a method for constructing a nucleus-implanted egg that is a nucleus-implanted having 2 haploid genome sets derived from ova of mammals and that is able to grow up to adulthood. According to the present invention, further, there are provided a method for constructing a parthenogenetic embryo from said nucleus-implanted egg and a method for producing a parthenogenetic mammal from said parthenogenetic embryo.

According to First invention, particularly, there can be provided the above nucleus-implanted egg having an ability to grow up to adulthood and a parthenogenetic embryo, and First invention is technically more significant than a conventional method in which a nucleus-implanted egg can be developed only up to a fetus approximately at day 13.5 of gestation.

The contents of First invention have been disclosed in a document (Tomohiro Kono et al, Nature Vol. 428. No. 6985, pp. 860-864, 22 Apr. 2004), after the filing of Japanese patent application No. 2003-286543 on which the priority of the present application is based.

Although First invention is an excellent method in that a nucleus-implanted egg having an ability to grow up to adulthood is obtained, the proportion of produced adults to parthenogenetic embryos is only about 1.5%, and an improvement in production efficiency of adults have been desired.

An object of Second invention is to provide a nucleus-implanted egg that is a nucleus-implanted egg having 2 (two) haploid genome sets derived from mammal ova and shows excellent production efficiency of adults. Another object of Second invention is to provide a method for constructing a parthenogenetic embryo from the nucleus-implanted egg and a method for producing a parthenogenetic mammal from the parthenogenetic embryo.

The fg ovum or ng ovum used in First invention is close to a gene derived from a sperm in that an imprinted gene, particularly an H19 gene, is missing. However, it differs from the gene derived from a sperm, and production efficiency of adults from an obtained nucleus-implanted egg is low.

Thus, we have focused our attention on paternal expressions and maternal expressions of genes and made studies for bringing a genomic gene of the second nucleus-implanted egg having 2 haploid genome sets derived from ova close to a genomic gene in the fertilization of sperm and ovum.

As a result, we have found that, in First invention, the production efficiency of adults can be improved significantly by use of an ovum in which both (A) a DNA methylation imprint region (region A) that controls expressions of H19 gene and Igf2 gene and (B) a DNA methylation imprint region (region B) that controls expressions of Gtl2 gene and Dlk1 gene are missing, as the ng ovum or fg ovum, and has completed an improved invention (call as 'Second invention') based on this finding.

According to Second invention, there is provided a method for constructing a nucleus-implanted egg of a mammal, the nucleus-implanted egg having a haploid genome set derived from an ng ovum and a haploid genome set derived from an fg ovum, which comprises the steps of (1) introducing a non-grown stage egg (ng ovum) into a nucleus-deleted egg in a germinal vesicle stage (GV stage egg) and then developing the obtained egg to an MII phase (second meiosis metaphase) by in vitro culture for development to prepare a first nucleus-implanted egg, and (2) extracting all of MII phase chromosomes from said first nucleus-implanted egg and introducing it into other MII phase egg (fg ovum) to prepare a second nucleus-implanted egg, wherein an ovum in which both (A) a DNA methylation imprint region (region A) that controls expressions of H19 gene and Igf2 gene and (B) a DNA methylation imprint region (region B) that controls expressions of Gtl2 gene and Dlk1 gene are missing is used as the ng ovum or fg ovum.

Further, Second invention includes a method for constructing a parthenogenetic embryo, which comprises activating said second nucleus-implanted egg and then developing the same in vitro culture for development.

Further, Second invention includes a method for producing a parthenogenetic mammal, which comprises implanting and growing said parthenogenetic embryo in the uterus of a female mammal.

The reason why the production efficiency of adults can be improved in Second invention can be estimated as follows. That is, in mammals, identical genes or alleles are arranged in the same sequence on homologous chromosomes derived from paternal and maternal genes, genic expressions are equally exhibited from biparental alleles to take part in gene expressions of individuals.

However, some genes exhibit paternal expressions and some genes exhibit maternal expressions. For example, an embryo growth factor Igf2 (insulin like growth factor II) gene is expressed from a paternal locus (derived from a sperm) but is not expressed from a maternal locus (derived from an ovum). Meanwhile, an H19 gene located in a downstream to the Igf2 gene is expressed only from a maternal locus. Such a gene is called an imprinted gene. This is because the Igf2 gene and the H19 gene have in common an enhancer (gene expression enhancing sequence) located in a downstream to the H19 gene. This enhancer generally works dominantly over the H19 gene, and when an expression regulating region (region A) in an upstream of the H19 gene undergoes gene modification posteriori (DNA methylation) during the generation of sperm, it can no longer work on the H19 gene, and it comes to work on the Igf2 gene. As a result, there is established a relationship in which the expression of the H19 gene from a paternal gene is inhibited and the Igf2 gene is expressed from a paternal gene.

Similarly, a Dlk1 gene and a Gtl2 gene are imprinted genes expressed from a paternal locus and a maternal locus, respectively. An expression regulating region (region B) located in an upstream of the Gtl2 gene undergoes methylation during the generation of sperm, whereby expression regulation is established.

That is, in the general fertilization of sperm and ovum, the H19 and Gtl2 genes are expressed from a maternal gene and the Igf2 and Dlk1 genes are expressed from a paternal gene, whereby normal embryogenesis is performed, as shown in Table 1.

TABLE 1

| Gene | Igf2 | H19 | Dlk1 | Gtl2 |
|---|---|---|---|---|
| Sperm | ○ | x | ○ | x |
| Ovum | x | ○ | x | ○ |

○: Expression is promoted.
x: Expression is inhibited.

In parthenogenesis between ova, it is expected that since the genes of both of the ova are derived from maternal genes, the H19 and Gtl2 genes expressed from a maternal gene are expressed excessively and the Igf2 and Dlk1 genes expressed from a paternal gene are not expressed, as shown in Table 2.

TABLE 2

| Gene | Igf2 | H19 | Dlk1 | Gtl2 |
|---|---|---|---|---|
| Ovum | x | ○ | x | ○ |
| Ovum | x | ○ | x | ○ |

○: Expression is promoted.
x: Expression is inhibited.

Thus, it is expected that when an ovum in which both the region A and the region B are missing is used as the ng ovum or fg ovum, expression regulation close to general fertilization of sperm and ovum is performed and an adult production rate can be improved significantly, as shown in Table 3.

TABLE 3

| Gene | Igf2 | H19 | Dlk1 | Gtl2 |
|---|---|---|---|---|
| Ovum Having No Regions A and B | ○ | x | ○ | x |
| Ovum | x | ○ | x | ○ |

○: Expression is promoted.
x: Expression is inhibited.

BRIEF DESCRIPTION OF DRAWINGS

In FIG. 1 to FIG. 4, symbols a to i represent as follows.
a: ng ovum derived from a neonate
b: fg ovum derived from a matured female
c: Nuclear implanting
d: Maturing in vitro by culturing
e: Matured nucleus-substituted ovum
f: Ovulation ovum
g: Implanting of MII phase mitotic apparatus
h: Artificial activation of ovum
i: Reconstructed ng/fg parthenogenetic embryo
a to e correspond to the first step of nuclear implantation in the present invention, and f to i correspond to the second step of nuclear implantation in the present invention.

BEST MODE OF EMBODIMENT OF THE INVENTION (First Step of Nuclear Implantation)

This is a step in which a primitive ovarian follicle ovum (ng ovum) is introduced into a nucleus-deleted germinal vesicle stage egg (GV stage egg) and matured in vitro by culturing to develop it up to MII phase (second meiosis metaphase).

As a GV stage egg, there can be used an in vivo grown ovum obtained by administering a matured mammal with a pregnant mare ciliary gonadotropic hormone and carrying out super-ovulation treatment or an in vivo grown ovum obtained from the ovary of a matured mammal without any treatment. The above in vivo grown ovum can be collected by incision of an ovarian follicle from a female mammal ovary obtained by super-ovulation treatment or without any treatment with an injection needle using a PBS solution or by suction from an ovarian follicle with an injection needle, or the like. In a GV stage egg having cumulus cells adhering thereto, preferably, the cumulus cells are removed by pipetting with a glass pipette or by oxygen treatment with trypsin-EDTA or the like.

The GV stage egg is subjected to the cutting of zona pellucida and deletion of nucleus to prepare a recipient egg. The zona pellucida can be cut off with a glass knife while observing it through a microscope. The deletion of nucleus can be performed by inserting a nucleus-deleting pipette through a zone pellucida ablation portion and removing it together with a small amount of cytoplasm.

While the ng ovum is preferably an oocyte in a fetal life or an oocyte of a neonate, it can be also collected from the ovary of a matured mammal.

The introduction is preferably carried out by cell fusion. Preferably, the ng ovum is injected into the subzone of the recipient egg together with Sendai virus of Japan (HVJ) and fused.

Then, the ng ovum is matured in vitro by culturing to be developed to MII phase (second meiosis metaphase). The maturation in vitro by culturing can be carried out in an αMEM culture medium containing 5% of fetal bovine serum (FBS) in a carbon dioxide culturing apparatus. There can be also sued an M16 culture medium containing 5% of fetal bovine serum (FBS). In the in vitro maturation by culturing, the egg performs the disintegration of karyotheca, the formation of a mitotic division apparatus, miosis and the releasing of the first polocyte, whereby there can be obtained the first nucleus-implanted egg that has reached MII phase.

The mammal preferably includes non-human animals such as a mouse, a swine, a cow, a sheep, a goat, a rat, a rabbit, and the like.

(Second Step of Nuclear Implantation)

This step is a step in which MII phase chromosome is extracted from the first nucleus-implanted egg and introduced into other MII phase egg (fg ovum) to prepare a second nucleus-implanted egg.

The fg ovum is preferably an ovulation ovum from a female matured mammal. The above ovulation ovum can be obtained by administering a matured mammal with a pregnant mare ciliary gonadotropic hormone or human ciliary gonadotropic hormone and carrying out ovulation treatment. On the other hand, as the fg ovum, there can be also used an egg that is developed to MII phase by obtaining an in vivo grown ovum from the ovary of a matured mammal without any treatment and maturing the ovum in a state where it is covered with cumulus cells by in vitro culturing. In the fg ovum, preferably, part of its zona pellucida is cut beforehand.

The introduction can be carried out by the following method. An MII phase chromosome (mitotic apparatus) is sucked from the zona pellucida ablation portion of the first nucleus-implanted egg with a nucleus-deleting pipette. Then, hemagglutinating virus of Japan is sucked in a tip of a pipette and injected into the MII phase chromosome by inserting the tip through the zone pellucida ablation portion of the fg ovum. These procedures are preferably carried out in a nuclear implanting medium such as an M2 culture medium. Then, culturing is carried out in the M2 culture medium for a pre-determined period of time for fusion, so that the second nucleus-implanted egg can be obtained. The second nucleus-implanted egg has a haploid genome set derived from the ng ovum and a haploid genome set derived from the fg ovum.

(Imprinted Gene)

In First invention, the ng ovum or the fg ovum is an ovum having, deleted, an imprinted gene that is to undergo gene modification posteriori during the spermatogenesis. The ng ovum or the fg ovum is preferably an ovum from which the imprinted gene and its expression regulating region are deleted.

The imprinted gene includes H19 gene (Leighton P. A. et al, Nature 375, 34-39, 1995), Igf2 gene (Leighton et al, Nature 375, 34-39, 1995), Dlk1 gene (Schmidt, J. V. et al, Genes Dev. 14, 1997-2002, 2000), Gtl2 gene (Schmidt, J. V. et al, Genes Dev. 14, 1997-2002, 2000) and Ras-grf1 gene.

It is therefore preferred to use an ovum from which at least one gene selected from the group consisting of H19, Igf2, Dlk1, Gtl2 and Ras-grf1 genes is deleted. It is more preferred to use an ovum from which at least one gene selected from the group consisting of H19, Gtl2 and Ras-grf1 genes is deleted. It is particularly preferred to use an ovum from which one or both of H19 and Gtl2 genes are deleted.

The ovum having the imprinted gene deleted can be obtained from a gene-deleted mammal. The gene-deleted mammal can be produced by the use of a known target gene recombination method (gene-targeting: e.g., Methods in Enzymology 225: 803-890, 1993), and for example, such a mouse can be obtained as follows.

First, the target sequence of an imprinted gene such as an isolated H19 gene, Gtl2 gene, or the like, is replaced with neomycin resistance gene ($Neo^r$ gene), and a thymidine kinase gene (HSV-tk gene) that is a herpes virus is added to the terminal portion of the imprinted gene to prepare a targeting vector. The targeting vector is introduced into mouse embryo-stem cells (ES cells), and there are selected cells in which the imprinted gene of cellular genome DNA is homologously recombined with the mutant sequence of the targeting vector.

The selection of the above gene-recombined cells can be made by adding G418 to a cell culture medium, removing non-recombined cells having no $Neo^r$ gene, further adding ganciclovir and removing random-recombined cells in which the HSV-tk gene remains. The imprinted gene of the thus-selected gene-recombined cells is a mutant sequence obtained by inserting the $Neo^r$ gene into the sequence thereof, and it cannot express the imprinted gene at all.

Then, the above gene-recombined ES cells are injected into the initial embryo (blastocyst) of a mouse, and the initial embryo is developed in vivo to an individual to produce a chimera mouse. And, the chimera mouse and a wild type mouse are allowed to mate to produce offspring mice, and individual mice having a mutant sequences in one or both of alleles are selected from the offspring mice, whereby gene-deleted mice can be obtained.

(Region A and Region B)

In Second invention, an ng ovum or fg ovum is an ovum in which both a region A and a region B are missing.

The region A is a DNA methylation imprint region that controls expressions of H19 gene and Igf2 gene. The region A is a region having a length of 10 kb and situated between the Igf2 gene and the H19 gene, in the case of a mouse. It is a region from an EcoRI restriction enzyme cleavage site nearest to the 5' side of the H19 gene to an EcoRI restriction enzyme cleavage site in an upstream of about 10 kb.

The H19 gene is described in Leighton P. A. et al, Nature 375, 34-39, 1995. The length of the H19 gene is 3 kb. The Igf2 gene is described in Leighton et al, Nature 375, 34-39, 1995.

The region B is a DNA methylation imprint region that controls expressions of Gtl2 gene and Dlk1 gene. The region B is a region having a length of 4.2 kb and situated between the Dlk1 gene and the Gtl2 gene, in the case of a mouse. It is a region from an Sca1 restriction enzyme cleavage site nearest to the 5' side of the Gtl2 gene to an Sac1 restriction enzyme cleavage site in an upstream of about 4.2 kb.

The Gtl2 gene is described in maternally expressed gene 3/gene-trap locus 2, Schmidt, J. V. et al, Genes Dev. 14, 1997-2002, 2000. The Dlk1 gene is described in Schmidt, J. V. et al, Genes Dev. 14, 1997-2002, 2000.

The ovum in which both the region A and the region B are missing can be obtained from neonates born by mating the respective gene-deleted mammals with each other. The gene-deleted mammal can be constructed by the use of a known target gene recombination method (gene-targeting: e.g., Methods in Enzymology 225: 803-890, 1993), and for example, such a mouse can be obtained as follows.

First, the target sequence of isolated regions A and B is replaced with a neomycin resistance gene (Neor gene), and a thymidine kinase gene (HSV-tk gene) that is a herpes virus is added to the terminal portion of the regions A and B to prepare a targeting vector. The targeting vector is introduced into mouse embryo-stem cells (ES cells), and there are selected cells in which the regions A and B of cellular genome DNA are homologously recombined with the mutant sequence of the targeting vector.

The selection of the above gene-recombined cells can be made by adding G418 to a cell culture medium, removing non-recombined cells having no Neor gene, further adding ganciclovir and removing random-recombined cells in which the HSV-tk gene remains. The regions A and B of the thus-selected gene-recombined cells are a mutant sequence obtained by inserting the Neor gene into the coding sequence thereof and cannot be expressed.

Then, the above gene-recombined ES cells are injected into the initial embryo (blastocyst) of a mouse, and the initial embryo is developed in vivo to an individual to produce a chimera mouse. Then, the chimera mouse and a wild-type mouse are allowed to mate to produce offspring mice, and individual mice having a mutant sequence in the regions A and B are selected from these offspring mice, whereby gene-deleted mice can be obtained.

Although Second invention uses an ovum in which the regions A and B that are expression regulating regions are missing, an ovum in which an H19 gene itself in addition to the regions A and B is missing may be used.

(Construction of Parthenogenetic Embryo)

The present invention includes a method for constructing a parthenogenetic embryo, which comprises activating the above second nucleus-implanted egg and then developing it in vitro by culturing. Preferably, the ovum is activated with strontium. Specifically, the ovum can be activated by culturing it in an M16 culture medium containing 10 mM of $SrCl_2$. Alternatively, the ovum can be activated by electric pulse, ethanol or the like. The development in vitro by culturing can be carried out under conditions of a 5% $CO_2$, 5% $O_2$ and 90% $N_2$ gaseous phase and 37 to 39° C.

(Production of Parthenogenetic Mammal)

The present invention includes a method for producing a parthenogenetic mammal, which comprises implanting the above parthenogenetic embryo in the uterus of a mammal and allowing it to grow. The mammal is naturally a same kind of mammal from which parthenogenetic embryo was constructed. While the mammal for the implantation is not specially limited, it is preferred to use a mammal that is artificially inseminated and then induced to abort with prostaglandin F2α, or the like during the early stage of gestation for synchronization. The mammal preferably includes non-human mammals such as a mouse, a swine, a cow, a sheep, a goat, a rat, a rabbit, and the like.

EXAMPLES

The present invention will be explained with reference to Examples hereinafter. In Examples, mice were used as a mammal.

Example 1

(Collection of ng Ova)

Ovaries were collected from one-day-old neonates of mice (Leighton et al, Nature 375: 34-39, 1995) from which 13 Kb of H19 genes and upstream regions thereof had been deleted according to a target gene recombination method (Methods in Enzymology 225: 803-890, 1993). The collected ovaries were transferred into a 0.02% EDTA solution and cultured at 37° C. for 10 minutes. Then, the ovaries were cut apart with an injection needle and dissociated non-grown stage ova were collected and used as ng ova as a donor.

(Collection of GV Stage Egg)

Matured mice (8 to 12 weeks old, B6D2F1, Charles River/Claire) were administered with pregnant mare ciliary gonadotropic hormone at a dose of 5 to 7.5 IU, and then grown ovarian follicles in the ovaries were cut apart with a 27-gage injection needle to collect GV stage eggs covered each with cumulus cells. The cumulus cells were removed by pipetting, and then the GV stage eggs were cultured in an M2 culture medium (containing 240 μM of dbcAMP and 5% FBS) at 37° C. for 2 hours.

(Nuclear Removal)

A micromanipulator (supplied by Narishige Co., Ltd.) was fixed to an inverted microscope for an operation. First, the zona pellucida each of the GV stage eggs was 15 to 20% cut off with a glass knife. Then, the GV stage eggs were transferred to a nucleus-implanting M2 medium (containing 10 μg/ml of cytochalasin B, 100 ng/ml of colcemid, 240 μM of dbcAMP and 5% FBS) and cultured at 37° C. for 15 minutes. By micromanipulation, a nucleus-removing pipette (having a diameter of 25 μm) was inserted through the ablation portion each of the zona pellucida, and the nucleus each of the GV stage eggs was removed together with a small amount of cytoplasm, to prepare recipient eggs.

(First Step of Nuclear Implantation)

Then, the ng ova were sucked into an implanting pipette (having a diameter of 15 μm), and then hemagglutinating virus of Japan (HVJ: Cosmobio) was sucked into the tip portion of the pipette. The pipette was inserted through the ablation portion of the zona pellucida each of the recipient eggs and pressed to each recipient egg for injection. The thus-obtained nucleus-implanted eggs were transferred to an αMEM culture medium containing 5% FCS and cultured in a carbon dioxide gas incubator at 37° C. for 14 hours. The nucleus-implanted eggs developed to the second meiosis metaphase (MII phase) through the steps of disintegration of the nuclear memblane, generation of the mitotic apparatus, miosis and releasing of the first polocyte, to give the first nucleus-implanted eggs.

(Second Step of Nuclear Implantation)

Matured female mice (8 to 12 weeks old, B6D2F1, Charles River/Claire) were administered with pregnant mare ciliary gonadotropic hormone and human ciliary gonadotropic hormone at a dose of 5 to 7.5 IU each at an interval of 48 hours, and 14 hours after the administration of the human ciliary gonadotropic hormone, oviducts were collected. A mass of ovulation ova covered with cumulus cells were collected from the oviducts, then, the cumulus cells were removed in an M2 culture medium containing 300 μg/ml of hyaluronidase by pipetting, and then, ovulation ova (fg ova) were collected. Part of zona pellucida was cut apart by micromanipulation. The ovulation ova and the first nucleus-implanted eggs were transferred into an implanting M2 culture medium (containing 5 μg/ml of cytochalasin B). A nucleus-deleting pipette (having a diameter of 25 μm) was inserted through the ablation portion of the zona pellucida each of the above first nucleus-implanted eggs, and MII phase chromosome (mitotic apparatus) was sucked therein. Then, hemagglutinating virus of Japan was sucked into the tip portion of the pipette, and the pipette was inserted into the ablation portion of zone pellucida each of the fg ova to inject MII phase chromosome. They were transferred to an M2 culture medium and cultured at 37° C. for 30 minutes to fuse them, whereby second nucleus-implanted eggs were obtained.

The following Table 4 shows production efficiency of the nucleus-implanted eggs.

TABLE 4

|  | First nucleus-implanted eggs | Second nucleus-implanted eggs |
| --- | --- | --- |
| Number of fused eggs/number of manipulated eggs (percent) | 287/350 (82%) | 212/249 (85%) |
| Number of maturation (percent) | 249 (87%) | — |

Example 2

(Construction of Parthenogenetic Embryo)

The thus-obtained 212 second nucleus-implanted eggs were cultured in an M16 culture medium containing 10 M of strontium chloride at 37° C. for 3 hours to artificially induce activation of the ova. As a result, 189 ova were activated. 158 Ova in which two each of the second polocytes and pronuclei were generated were in vitro cultured in an M16 culture medium at 37° C. for 3 days. As a result, 131 blastocysts were produced.

Example 3

(Production of Parthenogenetic Mouse)

The thus-obtained 131 blastocysts were implanted in an uterus of a female mouse at day 2.5 of pseudopregnancy (female mouse that was mated with a vasoligated male according to a conventional method and a day when its copulatory plug was confirmed was a day 0.5), to give birth to 2 normal female neonates. Analysis of genes of these showed that they had H19 gene (derived from the fg ovum) and Neo$^r$ gene (derived from ng ovum), so that it was confirmed that the above neonates were neonates from the second nucleus-implanted eggs.

Figure 1:
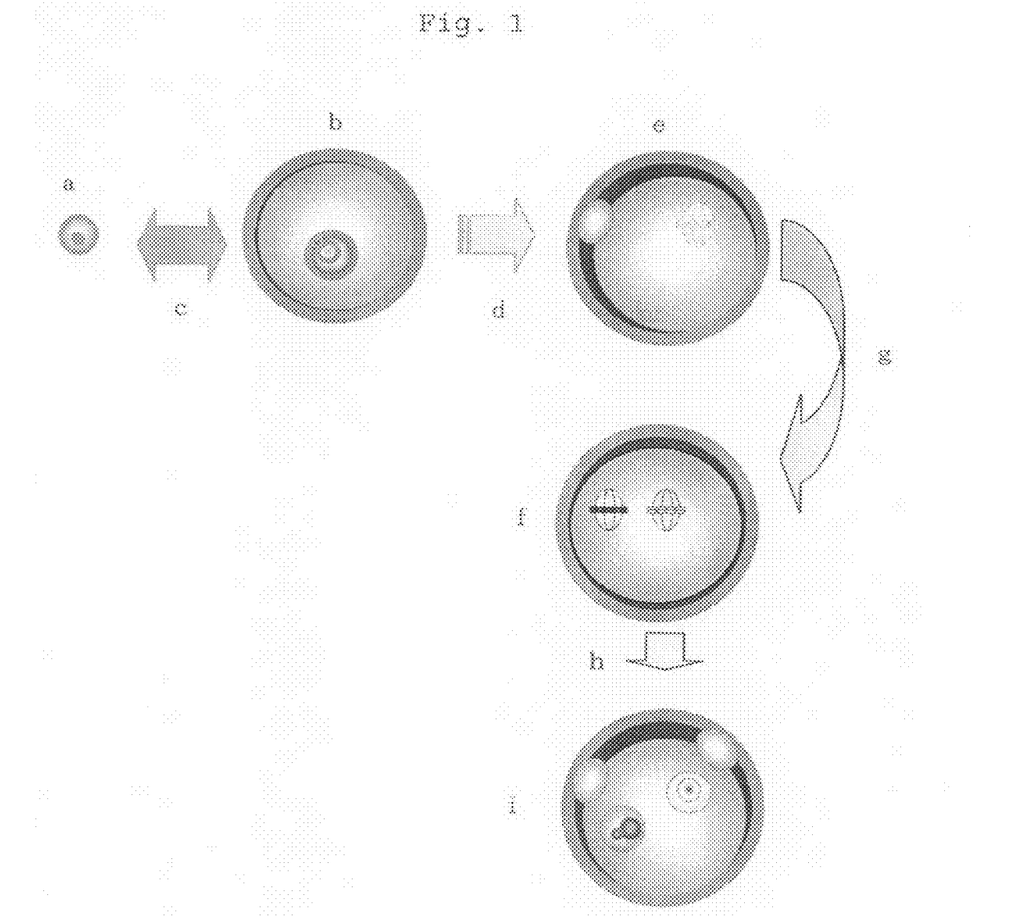
FIG. 1 is a drawing for schematically showing the method for constructing a nucleus-implanted egg, provided by First invention.
Figure 2:
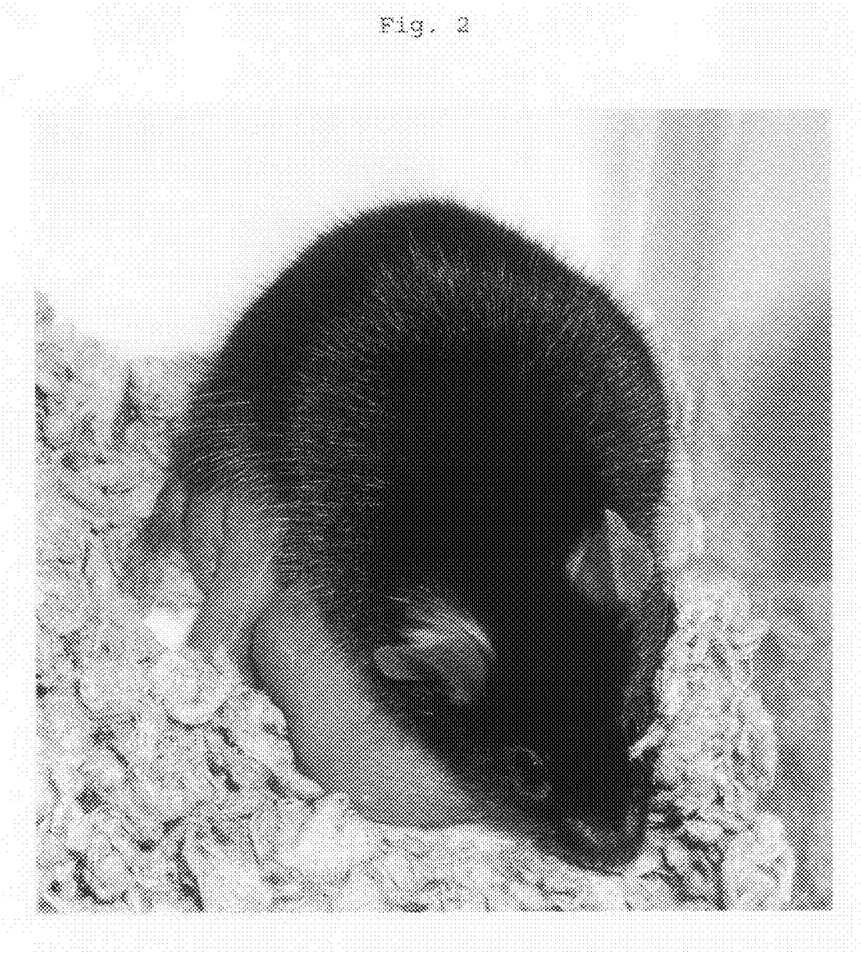
FIG. 2 is a photograph of a parthenogenetic mouse obtained according to First invention and an offspring thereof.
Figure 3:
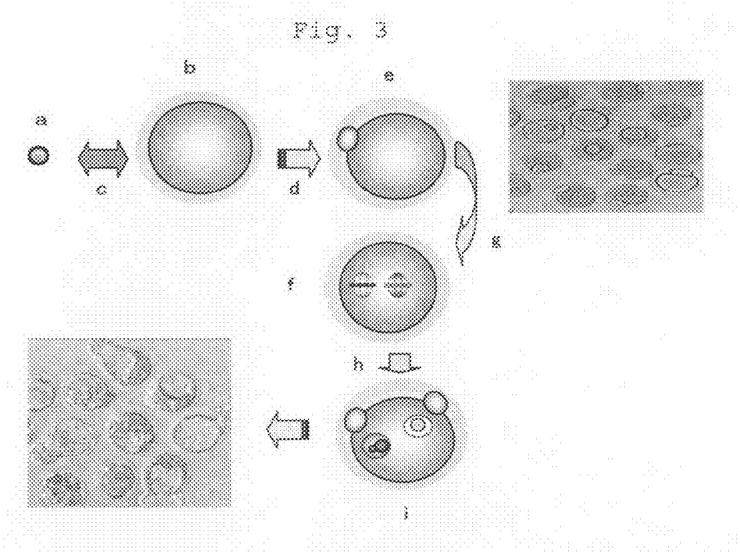
FIG. 3 is a drawing for schematically showing the method for constructing a nucleus-implanted egg, provided by Second invention.
Figure 4:
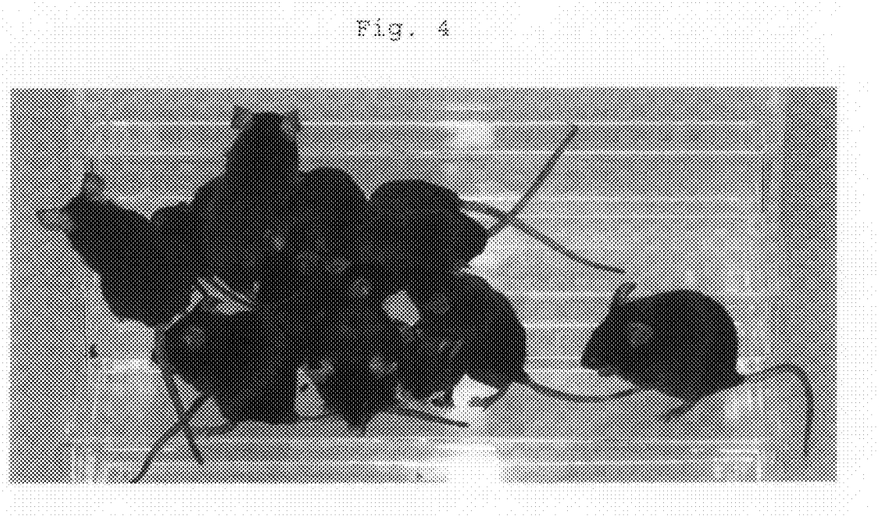
FIG. 4 is a photograph of a parthenogenetic mouse obtained according to Second invention and an offspring thereof.

One of these was sacrificed by euthanasia for gene analysis after its anabiosis was confirmed. The other one was named "Kaguya", and it normally grown to adulthood. "Kaguya" delivered neonates by mating with a male, so that it was confirmed that "Kaguya" had normal reproduction ability. FIG. 2 shows a photograph taken when "Kaguya" safely delivered the neonates.

Example 4

(Collection of ng Ova)

Ovaries were collected from one-day-old female neonates obtained by mating mice (Leighton et al., Nature 375: 34-39, 1995) from which 13 Kb (H19 genes and region A) of H19 genes (3 kb) and upstream regions thereof (10 kb) had been deleted according to a target gene recombination method (Methods in Enzymology 225: 803-890, 1993) with mice (Schmidt, J. V. et al, Genes Dev. 14, 1997-2002, 2000) from which a Dlk1-Gtl2 expression regulating region (region B, length: 4.15 Kb, Gtl2 gene upstream regions) had been deleted. The collected ovaries were transferred into a 0.02% EDTA solution and cultured at 37° C. for 10 minutes. Then, the ovaries were cut apart with an injection needle and dissociated non-grown stage ova where collected. Ova from which both the region A and the region B had been deleted were selected from the obtained ova and used as ng ova as a donor.

(Collection of GV Stage Egg)

Matured mice (8 to 12 weeks old, B6D2F1, Charles River/Claire) were administered with pregnant mare ciliary gonadotropic hormone at a dose of 5 to 7.5 IU, and then grown ovarian follicles in the ovaries were cut apart with a 27-gage injection needle to collect GV stage eggs covered each with cumulus cells. The cumulus cells were removed by pipetting, and then the GV stage eggs were cultured in an M2 culture medium (containing 240 μM of dbcAMP and 5% FBS) at 37° C. for 2 hours.

(Nuclear Removal)

A micromanipulator (supplied by Narishige Co., Ltd.) was fixed to an inverted microscope for an operation. First, the zona pellucida each of the GV stage eggs was 15 to 20% cut off with a glass knife. Then, the GV stage eggs were transferred to a nucleus-implanting M2 medium (containing 10 μg/ml of cytochalasin B, 100 ng/ml of colcemid, 240 μM of dbcAMP and 5% FBS) and cultured at 37° C. for 15 minutes. By micromanipulation, a nucleus-removing pipette (having a diameter of 25 μm) was inserted through the ablation portion each of the zona pellucida, and the nucleus each of the GV stage eggs was removed together with a small amount of cytoplasm, to prepare recipient eggs.

(First Step of Nuclear Implantation)

Then, the ng ova were sucked into an implanting pipette (having a diameter of 15 μm), and then hemagglutinating virus of Japan (HVJ: Cosmobio) was sucked into the tip portion of the pipette. The pipette was inserted through the ablation portion of the zona pellucida each of the recipient eggs and pressed to each recipient egg for injection. The thus-obtained nucleus-implanted eggs were transferred to an αMEM culture medium containing 5% FCS and cultured in a carbon dioxide gas incubator at 37° C. for 14 hours. The nucleus-implanted eggs developed to the second meiosis metaphase (MII phase) through the steps of disintegration of the nuclear membrane, generation of the mitotic apparatus, miosis and releasing of the first polocyte, to give the first nucleus-implanted eggs.

(Second Step of Nuclear Implantation)

Matured female mice (8 to 12 weeks old, B6D2F1, Charles River/Claire) were administered with pregnant mare ciliary gonadotropic hormone and human ciliary gonadotropic hormone at a dose of 5 to 7.5 IU each at an interval of 48 hours, and 14 hours after the administration of the human ciliary gonadotropic hormone, oviducts were collected. A mass of ovulation ova covered with cumulus cells were collected from the oviducts, then, the cumulus cells were removed in an M2 culture medium containing 300 μg/ml of hyaluronidase by pipetting, and then, ovulation ova (fg ova) were collected. Part of zona pellucida was cut apart by micromanipulation. The ovulation ova and the first nucleus-implanted eggs were transferred into an implanting M2 culture medium (containing 5 μg/ml of cytochalasin B). A nucleus-deleting pipette (having a diameter of 25 μm) was inserted through the ablation portion of the zona pellucida each of the above first nucleus-implanted eggs, and an MII phase chromosome (mitotic apparatus) was sucked therein. Then, hemagglutinating virus of Japan was sucked into the tip portion of the pipette, and the pipette was inserted into the ablation portion of zone pellucida each of the fg ova to inject the MII phase chromosome. They were transferred to an M2 culture medium and cultured at 37° C. for 30 minutes to fuse them, whereby second nucleus-implanted eggs were obtained.

The following Table 5 shows production efficiency of the nucleus-implanted eggs.

TABLE 5

|  | First Nucleus-Implanted Eggs | Second Nucleus-Implanted Eggs |
|---|---|---|
| Number of Fused Eggs/Number of Manipulated Eggs (percent) | 322/383 (84.1%) | 238/274 (86.9%) |
| Number of Mature Eggs (percent) | 274 (85.1%) | — |

Example 5

(Construction of Parthenogenetic Embryo)

The thus-obtained 238 second nucleus-implanted eggs were cultured in an M16 culture medium containing 10 M of strontium chloride at 37° C. for 3 hours to artificially induce activation of the ova. As a result, 221 ova were activated. The ova were in vitro cultured in an M16 culture medium at 37° C. for 3 days. As a result, 206 blastocysts were produced.

Example 6

(Production of Parthenogenetic Mouse)

The thus-obtained 206 blastocysts were implanted in an uterus of a female mouse at day 2.5 of pseudopregnancy (female mouse that was mated with a vasoligated male according to a conventional method and a day when its copulatory plug was confirmed was a day 0.5), to give birth to 14 normal female neonates, all of which grew to adulthood. Thus, production efficiency was as high as 7%. Analysis of their genes showed that they had deficiencies of expression regulating methylation regions (regions A and B) of H19-IGF2 gene and GTL-DLK1 gene in hetero, so that it was confirmed that the above neonates were neonates from the second nucleus-implanted eggs.

As a result of examining the reproduction abilities of five mice out of these 14 parthenogenetic mice, it was found that all of the tested parthenogenetic mice normally mated, became pregnant and gave birth and it was confirmed that they all had a normal reproduction ability.

Advantageous Effects of Invention

According to First invention, there can be constructed an adult parthenogenetic mammal having 2 haploid genome sets derived from ova.

According to Second invention, there is provided a method for constructing a nucleus-implanted egg that is a nucleus-implanted egg having 2 haploid genome sets derived from mammal ova and shows excellent production efficiency of adults. Further, according to Second invention, there are also provided a method for constructing a parthenogenetic embryo from the nucleus-implanted egg and a method for producing a parthenogenetic mammal from the parthenogenetic embryo. Mammals obtained by the present invention have a normal reproduction ability.

In particular, according to Second invention, production efficiency of adults with respect to a parthenogenetic embryo is about 7%, and the present invention is technically more significant than First invention showing a production efficiency of about 1.5%.

INDUSTRIAL UTILITY

According to the present invention, there can be produced an adult parthenogenetic mammal having 2 haploid genome sets derived from ova. Such a mammal is useful as a laboratory animal for analyzing functions of genes. According to the present invention, obtained mammals are all female, so that there can be efficiently produced, for example, milking cows that have excellent genes and that are genetically uniform. Further, there can be efficiently produced cows that provide excellent beef cattle. The present invention so promises its use in the livestock industry. In case parthenogenetic mammals are produced according to the present invention, non-human mammals are main objects thereof, while it is expected that the present invention will be applied to production of internal organs for implantation in the medical field.

The invention claimed is:

1. A method for constructing a nucleus-implanted egg of a mouse, the nucleus-implanted egg having a haploid genome set derived from ng ovum and a haploid genome set from fg ovum, which comprises the steps of
   (1) introducing a mouse primitive ovarian follicle egg (ng ovum) into a mouse nucleus-deleted egg in a germinal vesicle stage (GV stage egg) and then developing the obtained egg to MII phase (second meiosis metaphase) by in vitro maturing and culturing to prepare a first nucleus-implanted egg, and
   (2) extracting all of MII phase chromosome from said first nucleus-implanted egg and introducing said MII phase chromosomes into a second mouse MII phase egg (fg ovum) to prepare a second nucleus-implanted egg,
   wherein ovum from which the 13 kb totaled H19 genes and upstream regions thereof that undergoes epigenetic modification during the generation of sperm is deleted is used as the ng ovum or fg ovum.

2. The method of claim 1, wherein the primitive ovarian follicle egg (ng ovum) is an oocyte of a neonate.

3. The method of claim 1, wherein the second MII phase egg is an ovulation ovum.

4. A method for constructing a parthenogenetic mouse embryo, which comprises activating the second nucleus-implanted egg obtained by the method recited in claim 1 and then culturing the second nucleus-implanted egg in vitro to develop the second nucleus-implanted egg.

5. A method for producing a parthenogenetic mouse, which comprises implanting the parthenogenetic embryo obtained by the method recited in claim 4 into the uterus of a mouse and growing the parthenogenetic embryo.

6. A method for constructing a nucleus-implanted egg of a mouse, the nucleus-implanted egg having a haploid genome set derived from an ng ovum and a haploid genome set derived from an fg ovum, which comprises the steps of
   (1) introducing a non-grown stage mouse egg (ng ovum) into a mouse nucleus-deleted egg in a germinal vesicle stage (GV stage egg) and then developing the obtained egg to an MII phase (second meiosis metaphase) by in vitro culture for development to prepare a first nucleus-implanted egg, and
   (2) extracting all of MII phase chromosomes from said first nucleus-implanted egg and introducing said MII phase chromosomes into a second mouse phase egg (fg ovum) to prepare a second nucleus-implanted egg,
   wherein an ovum in which both (A) a DNA methylation imprint region (region A) that controls expressions of H19 gene and Igf2 gene and (B) a DNA methylation imprint region (region B) that controls expressions of Gtl2 gene and Dlk1 gene are deleted is used as the ng ovum or fg ovum.

7. The method of claim 6, wherein the non-grown stage egg (ng ovum) is an oocyte of a neonate.

8. The method of claim 6, wherein the second MII phase egg (fg ovum) is an ovulation ovum.

9. A method for constructing a parthenogenetic mouse embryo, which comprises activating the second nucleus-implanted egg obtained by the method recited in claim 6 and then culturing the second nucleus-implanted egg in vitro to develop the second nucleus-implanted egg.

10. A method for producing a parthenogenetic mouse, which comprises implanting the parthenogenetic embryo obtained by the method recited in claim 9 into the uterus of a mouse and growing the parthenogenetic embryo.

* * * * *